United States Patent
Bentzel

(10) Patent No.: US 7,500,396 B2
(45) Date of Patent: Mar. 10, 2009

(54) PHASED ARRAY ULTRASONIC METHODS AND SYSTEMS FOR GENERATOR ROTOR TEETH INSPECTION

(75) Inventor: Edward Lee Bentzel, Latham, NY (US)

(73) Assignee: General Electric Company, Schenectady, NY (US)

( * ) Notice: Subject to any disclaimer, the term of this patent is extended or adjusted under 35 U.S.C. 154(b) by 399 days.

(21) Appl. No.: 11/254,521

(22) Filed: Oct. 20, 2005

(65) Prior Publication Data

US 2007/0089517 A1    Apr. 26, 2007

(51) Int. Cl.
*G01N 29/00*   (2006.01)
(52) U.S. Cl. .......................................... 73/628; 73/660
(58) Field of Classification Search ................... 73/628, 73/660
See application file for complete search history.

(56) References Cited

U.S. PATENT DOCUMENTS

| | | | |
|---|---|---|---|
| 4,170,145 A | 10/1979 | Kennedy et al. | |
| 4,457,176 A | 7/1984 | Scholz | |
| 4,757,716 A * | 7/1988 | Nottingham et al. | 73/623 |
| 4,864,862 A * | 9/1989 | Nottingham et al. | 73/623 |
| 4,901,578 A | 2/1990 | Brill, III | |
| 4,964,295 A * | 10/1990 | Nottingham et al. | 73/597 |
| 4,991,427 A * | 2/1991 | Nottingham et al. | 73/623 |
| 4,991,441 A * | 2/1991 | Nottingham et al. | 73/633 |
| 5,319,844 A | 6/1994 | Huang et al. | |
| 5,382,859 A | 1/1995 | Huang et al. | |
| 5,710,378 A | 1/1998 | Dykes et al. | |
| 5,969,531 A | 10/1999 | Murakami et al. | |
| 6,082,198 A * | 7/2000 | Sabourin et al. | 73/633 |
| 6,487,922 B1 | 12/2002 | Bauer et al. | |
| 6,736,011 B2 * | 5/2004 | Zayicek et al. | 73/628 |
| 6,849,972 B1 | 2/2005 | Barnes et al. | |

(Continued)

FOREIGN PATENT DOCUMENTS

GB    2263777 A    4/1993

(Continued)

OTHER PUBLICATIONS

A. Erhard, et al., Calculation and Construction of Phased Array-UT Probes, Nuclear Engineering and Design 94:375-385 (1986).

(Continued)

*Primary Examiner*—Hezron E. Williams
*Assistant Examiner*—Samir M. Shah
(74) *Attorney, Agent, or Firm*—Armstrong Teasdale LLP

(57) ABSTRACT

Methods and systems for inspecting a generator rotor is provided. The system includes a phased-array ultrasound transducer that includes an active face including a plurality of transducer elements formed in an array, the elements are configured to be excited in a predetermined sequence to generate a transmission beam of ultrasound energy at a plurality of angles with respect to the active face. The elements are configured to receive ultrasound echoes through the active face. The system also includes a transducer wedge including a coupling face configured to couple to the transducer and a transmission face configured to couple to the rotor. The wedge is configured to refract the ultrasound transmission beam at a predetermined angle at the transmission face such that the beam enters the component at an angle substantially normal to a load surface of the rotor.

17 Claims, 3 Drawing Sheets

U.S. PATENT DOCUMENTS

| | | | |
|---|---|---|---|
| 6,857,330 B2 * | 2/2005 | Murphy et al. | 73/865.8 |
| 7,098,560 B2 | 8/2006 | Humphries et al. | |
| 7,275,441 B2 * | 10/2007 | Bentzel | 73/643 |
| 7,275,442 B2 * | 10/2007 | Bentzel | 73/643 |
| 2005/0264124 A1 | 12/2005 | Zhang et al. | |

FOREIGN PATENT DOCUMENTS

| | | |
|---|---|---|
| JP | 2001116728 A | 1/2004 |

OTHER PUBLICATIONS

EP Search Report, App. No. 06255318.5 (Jan. 25, 2007).

* cited by examiner

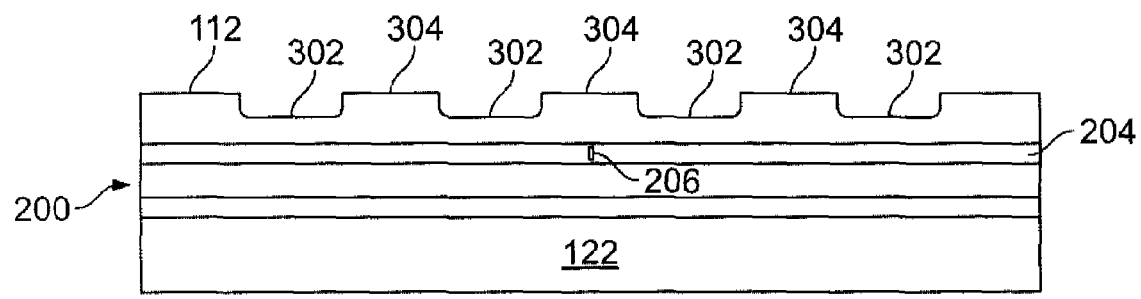
FIG. 3
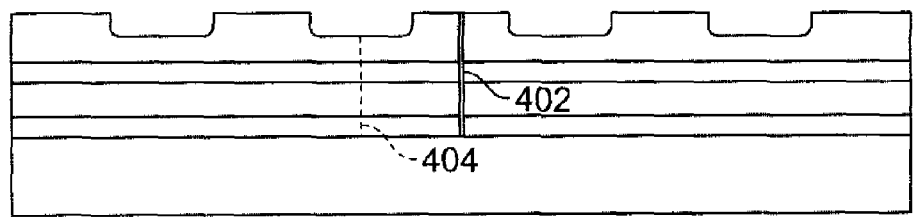
FIG. 4
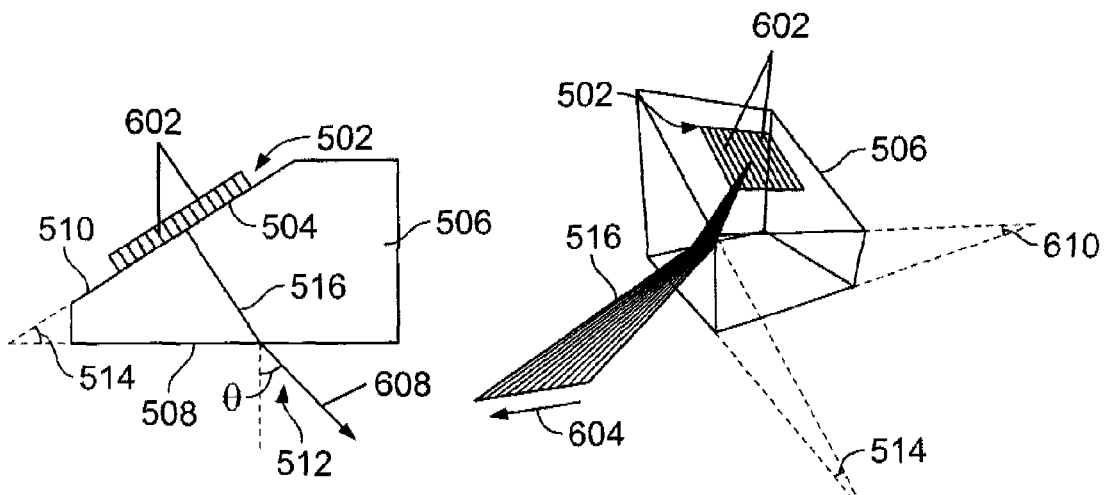
FIG. 5
FIG. 6

PHASED ARRAY ULTRASONIC METHODS AND SYSTEMS FOR GENERATOR ROTOR TEETH INSPECTION

BACKGROUND OF THE INVENTION

This invention relates generally to electrical power generators and more particularly, to methods and systems for inspecting electrical power generator components.

Conventional dynamoelectric machines, such as generators used with gas and steam turbines, employ forged rotors of magnetic material into which radial slots are machined along the axial length of the rotor for receiving the conductive turns of field windings which are interconnected such as to produce a desired magnetic flux pattern. Typically, included in such conventional rotor slots are creepage blocks at both the top and bottom ends of the slot as well as coil slot wedges for resisting the radially outward forces exerted on the windings when the rotor is operational.

The slot wedges, which are generally dovetail shaped, are used to maintain the copper coils in place while the rotor is spinning at, for example, 3600 revolutions per minute. In known rotors, coil slot wedges are approximately six to twelve inches long with a number of such wedges being used for each coil slot, particularly in the longer rotors with high electrical ratings. In an effort to decrease the number of parts that are required for assembly as well as increasing the overall speed of such assembly, full length wedges have been used in certain applications. For other applications, tolerances preclude the use of full length wedges and, in these cases, two or more wedges are used in each rotor slot. Cracks have been found, however, in the dovetail region of slot walls of several generators, at the butt joint between adjacent rotor wedges, apparently due to fretting damage found at the ends of steel wedges. Over time, such cracks may grow and affect the performance of the rotor.

Known inspection techniques are limited in their ability to assess the integrity of the rotor tooth dovetails while the rotor is in place. More specifically, a visual inspection only permits a limited examination of the rotor tooth for cracks. The rotor tooth is the structure present between adjacent rotor slots. To thoroughly examine the rotor tooth dovetails where cracking may originate, at least a portion of the generator casing may need to be removed to facilitate removal of the rotor and potentially the rotor wedges, and subsequent inspection of the dovetails with visual, magnetic particle, liquid penetrant, or eddy current techniques. However, because of labor and cost constraints such techniques may be impracticable in some instances.

BRIEF DESCRIPTION OF THE INVENTION

In one embodiment, a system for inspecting a generator rotor includes a phased-array ultrasound transducer that includes an active face including a plurality of transducer elements formed in an array, the elements are configured to be excited in a predetermined sequence to generate a transmission beam of ultrasound energy at a plurality of angles with respect to the active face. The elements are configured to receive ultrasound echoes through the active face. The system also includes a transducer wedge including a coupling face configured to couple to the transducer and a transmission face configured to couple to the rotor. The wedge is configured to refract the ultrasound transmission beam at a predetermined angle at the transmission face such that the beam enters the component at an angle substantially normal to a load surface of the rotor.

In another embodiment, a method of inspecting a rotor of an electrical generator includes coupling an active face of an ultrasound transducer to a substantially wedge-shaped shoe wherein the transducer includes a plurality of transducer elements formed in an array, exciting the plurality of transducer elements to generate an ultrasonic transmission beam, and transmitting the ultrasonic beam through the shoe such that the ultrasonic beam is refracted to an angle substantially normal to a load surface in the rotor.

In yet another embodiment, a method of inspection of an electrical generator rotor includes positioning an active face of an ultrasound transducer along a surface of the generator rotor wherein the transducer includes a plurality of transducer elements formed in an array, exciting the plurality of transducer elements to produce an ultrasonic transmission beam transmitted into the generator rotor along a selected ray path from the array, receiving a plurality of echo signals from the generator rotor using the transducers as receive elements, and determining a density interface indicative of a crack in the generator rotor using the plurality of echo signals.

BRIEF DESCRIPTION OF THE DRAWINGS

FIG. 3 is a schematic side view of the tooth shown in FIG. 2;

FIG. 4 is a schematic side view of the wedge shown in FIG. 2;

FIG. 5 is a schematic side view of an exemplary ultrasound transducer configuration that may be used to identify and locate cracks in the dovetail load surface shown in FIG. 2;

FIG. 6 is a schematic 3D view of the ultrasound transducer configuration shown in FIG. 5;

DETAILED DESCRIPTION OF THE INVENTION

Figure 1:
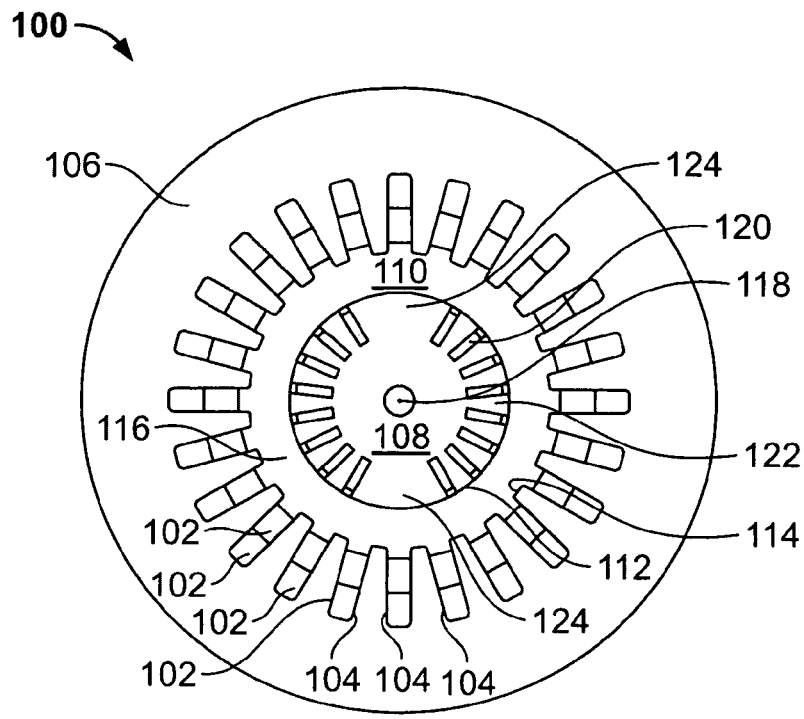
FIG. 1 is a schematic end view of an exemplary electric generator.

FIG. 1 is a schematic end view of an exemplary electric generator 100. A plurality of stator bar windings 102 are positioned in slots 104 defined around an inner circumference of a stator core 106. In the exemplary embodiment, stator bar windings 102 are formed from a plurality of flat bar conductors or stator bars that are coupled together to form a predetermined winding path through winding 102. In one embodiment, the stator bars are fabricated from copper. A rotor 108 is coaxially aligned with a bore 110 of stator core 106. An outer periphery 112 of rotor 108 is spaced apart from an inner periphery 114 of stator core 108 by an air gap 116. Rotor 108 is rotatable about a longitudinal axis 118 (illustrated into and out of FIG. 1). A plurality of rotor, or field slots 120 and field teeth 122 are alternately spaced about outer periphery 112. Field slots 120 are configured to receive field conductors (not shown) that carry field current such that a magnetic excitation field is generated at poles 124 spaced about outer periphery 112.

During operation, rotor 108 is rotated about axis 118 by a prime mover, such as a turbine or engine. Field current flowing in the conductors induces a magnetic field at poles 124, which rotate with rotor 108. The lines of flux of the magnetic fields interact with the stator conductors to generate an electric potential in the stator conductors, which induces a current flow that is transmitted to supply an electrical load coupled to generator 100.

Figure 2:
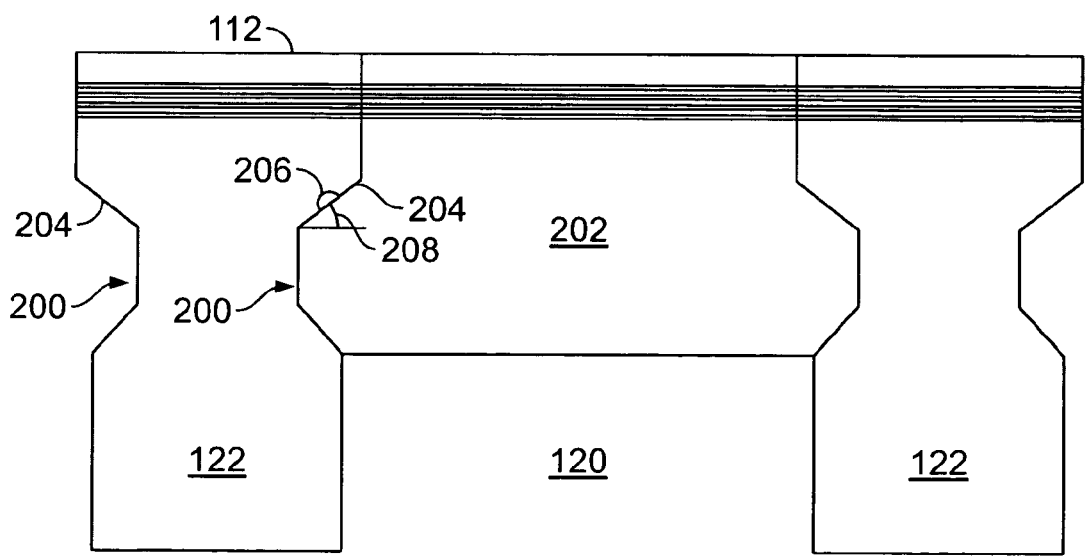
FIG. 2 is an enlarged schematic end view of the electric generator illustrating one of the plurality of rotor teeth and an adjacent slot.

FIG. 2 is an enlarged schematic end view of electric generator 100 illustrating one of the plurality of rotor teeth 122 and an adjacent slot 120. Tooth 122 includes a cutout 200 shaped to be complementary to a dovetail shape of a wedge 202. Wedges 202 have a generally dovetail shape in cross section, and are positioned and configured to maintain rotor coils and creepage blocks (both not shown in FIG. 2) substantially fixed in place while rotor 108 is rotating. Cutout 200 includes a dovetail load surface 204 that bears a portion of the centrifugal loading of wedge 202 and the rotor coils and creepage blocks. Load forces bearing on dovetail load surface 204, over time, tend to induces cracks 206 in dovetail load surface 204. For example, axial movement of wedges 202 during operation causes relative movement across the butt joint of two adjacent wedges 202. Over time, such relative movement causes fretting on dovetail load surface 204 constraining the outward radial movement of wedges 202. The fretting action on the dovetail load surface 204 at the butt joints can induce cracking at this location. Another possible source of cracking on the load surface in the vicinity of the butt joints is electrical arcing between wedges 202 and generator field. An angle 208 defines the angle of dovetail load surface 204 with respect to tooth surface 112.

FIG. 3 is a schematic side view of tooth 122 shown in FIG. 2. Tooth 122 includes a plurality of grooves 302 machined into outer periphery 112. Grooves 302 extend circumferentially about outer periphery 112 and extend through teeth 122 and adjacent wedges 202 such that grooves 302 in teeth 122 are in substantial alignment with grooves 302 in wedges 202 (not shown in FIG. 3). The portion of outer periphery 112 between grooves 302 are known as lands 304.

FIG. 4 is a schematic side view of wedge 202 shown in FIG. 2. Wedges 202 typically do not extend the entire length of rotor 108, but rather are configured as a series of segments butted end to end within slot 120. As such wedges 202 may be butted together at a butt joint 402 or may butted together at a butt joint 404. Cracks caused by fretting generally occur in the vicinity of the butt joints. In the case of a butt joint coinciding with the center of land 402, the crack occurs proximate the butt joint near the center of the land. In the case of a butt joint coinciding with the center of groove 404, the crack occurs proximate the butt joint at the center of the groove.

FIG. 5 is a schematic side view of an exemplary ultrasound transducer configuration that may be used to identify and locate cracks in dovetail load surface 204 (shown in FIG. 2). In one embodiment, an ultrasound transducer 502 is positioned such that an active face 504 of transducer 502 is mated to outer periphery 112 through a mating shoe 506. In the exemplary embodiment, shoe 506 includes a first surface 508 that substantially matches the contour of rotor teeth 122. In alternative embodiments, where the diameter of rotor 108 is relatively large, surface 508 is flat. A second surface 510 is configured to couple to active face 504 such that the angle of surface 510 affects an angle of refraction 512 of the ultrasonic beam in tooth 122 (not shown in FIG. 5). A "roof" angle 514 of surface 510 with respect to surface 508 is selected such that angle 514 causes an ultrasound beam 516 to be refracted substantially perpendicular to dovetail load surface 204 (shown in FIG. 2).

FIG. 6 is a schematic 3D view of the ultrasound transducer configuration shown in FIG. 5. Transducer 502 includes a plurality of transducer elements 602 arranged in a linear array such that by selectively exciting various ones of the plurality of transducer elements 602, ultrasound beam 516 is directed along a corresponding path in teeth 122. During operation of transducer 502, the ultrasound pulse emitted from each of transducer elements 602 is controllable to coordinate and sequence the emission at each transducer elements 602. By applying delays to the pulses from successive elements 602 in the linear phased array transducer 502 a beam is generated that sweeps along the dovetail load surface 204 (shown in FIG. 2) in a direction 604 to the right or an opposite direction 606 to the left. For example, by timing the excitation of the plurality of transducers elements 602, transmission beam 516 is directed towards a first point on the load surface of teeth 122. By varying the excitation parameters associated with the plurality of transducer elements 602, the transmission beam is swept in an axial direction along the load surface of teeth 122 to a second point. Echoes received while the transmission beam is swept from the first point to the second point are analyzed to determine the presence of crack indications within teeth 122.

In the exemplary embodiment, transducer 502 is mounted on shoe 506 such that beam 516 produced by the combination of individual elements 602 is refracted nominally perpendicular to dovetail load surface 204. The linear array of elements is oriented parallel to the axial direction of the tooth. Beam 516 is swept in an axial direction along dovetail load surface 204. The cracks on dovetail load surface 204 that are oriented in a circumferential-radial plane are detectable using this method. Beam 516 is swept in the axial direction to create an optimal reflection from the crack back to the transducer 502 for detection. A direction 608 is the direction that the beam is refracted (shown by angle 512 in FIG. 5).

In the exemplary embodiment, shoe 506 is formed as a compound wedge shape wherein surface 510 is cut at two angles, for example, a "wedge" angle 610 and "roof" angle 514. Wedge angle 610 is cut relative to the active axis of transducer 502. Wedge angle 610 influences the range of angles, in direction 604, through which beam 516 is laterally steered along the load surface of field tooth 122. Roof angle 514 is cut relative to the passive axis of transducer 502 and influences the nominal angle beam 516 strikes load surface 204. The combined effect of angles 514 and 610 determines the trajectory of beam 516 as it is travels in a largely axial direction along the load surface 204. To steer beam 516 in the opposite axial direction, wedge angle 610 is cut in the opposite side of shoe 506.

Figure 7:
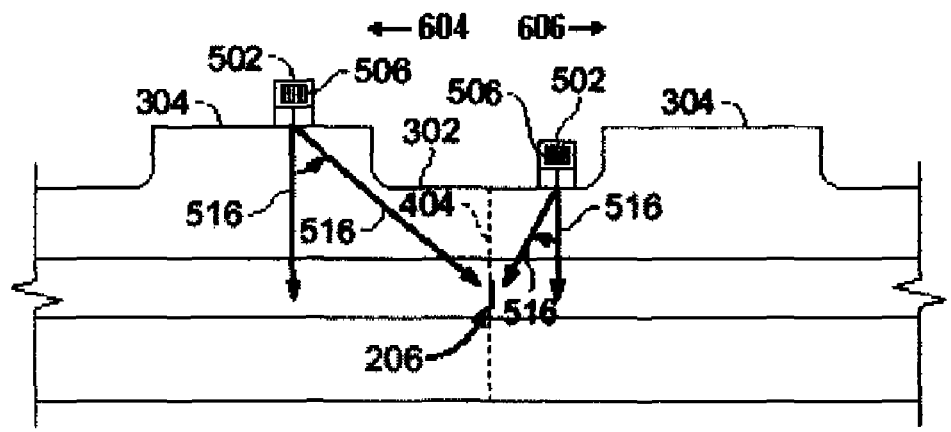
FIG. 7 is a schematic side view of the tooth shown in FIG. 2.

FIG. 7 is a schematic side view of tooth 122 shown in FIG. 2. Linear phased array transducer 502 is positionable in different positions to detect crack 506 when a butt joint occurs at center of groove 302. Wedge butt joints occur either at an axial center of land 304 or an axial center of groove 302. In the exemplary embodiment, the wedge butt joint is illustrated at the center of groove 302. The butt joint locations are where cracks resulting from fretting typically occur. In the exemplary inspection method linear phased array transducer 502 probe is manually positioned adjacent to butt joint 404. Beam 516 is swept toward butt joint 404 to inspect the area for cracking. Transducer 502 is used to perform the inspection positioned in groove 302 or alternatively on land 304. Additionally, the inspection is performed from both sides of butt joint 404 from groove 302 or land 304.

Figure 8:
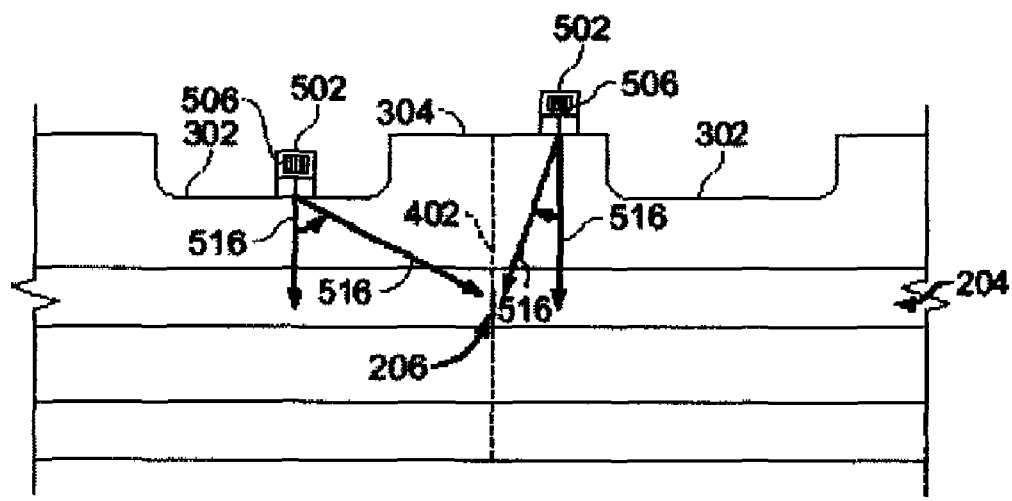
FIG. 8 is another schematic side view of the tooth shown in FIG. 2.

FIG. 8 is a schematic side view of tooth 122 shown in FIG. 2. Linear phased array transducer 502 is positionable in different positions to detect crack 506 when a butt joint occurs at center of land 304. Wedge butt joints occur either at an axial center of land 304 or an axial center of groove 302. In the exemplary embodiment, the wedge butt joint is illustrated at the center of land 304. In the exemplary inspection method linear phased array transducer 502 probe is manually positioned adjacent to butt joint 402. Beam 516 is swept toward butt joint 402 to inspect the area for cracking. Transducer 502 is used to perform the inspection positioned in groove 302 or alternatively on land 304. Additionally, the inspection is performed from both sides of butt joint 402 from groove 302 or land 304.

Figure 9:
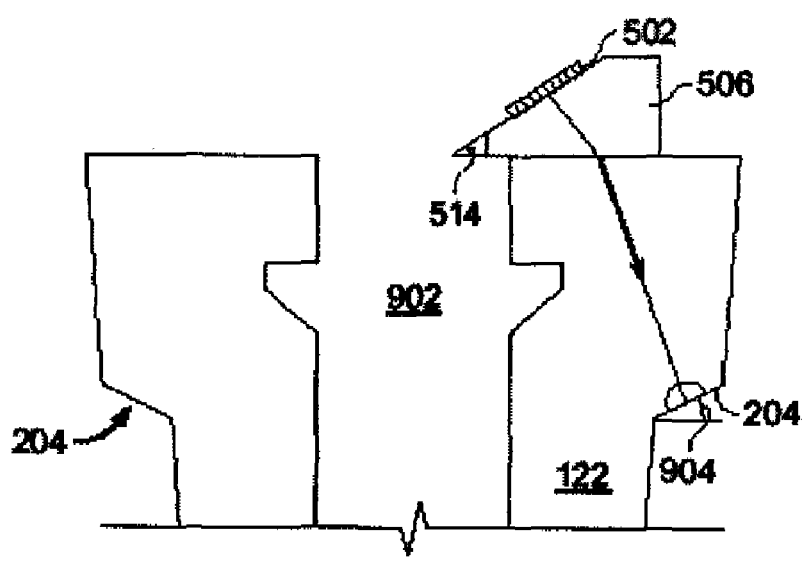
FIG. 9 is a schematic side view of an exemplary tooth with a uniform tooth surface.

FIG. 9 is a schematic side view of an exemplary tooth with a uniform tooth surface. The present inspection method is applicable to a wide variety of field tooth designs. In the exemplary embodiment, the generator field tooth design does not include the series of lands and grooves on the outer surface of the tooth. The exemplary embodiment includes a vent slot 902 for cooling in the center of the tooth. In various alternative embodiments, the generator field tooth design does not include vent slot 902. When the tooth surface is substantially uniform the inspection to identify and locate cracking is relatively simpler because there are no grooves and lands restricting the location transducer 502 can be positioned. In each configuration of a rotor tooth, a shoe is used that is configured to produce a refracted ultrasound beam substantially normal to dovetail load surface 204. Whenever dovetail load surface 204 changes from one tooth design to another, a different shoe 506 is used to produce a refracted ultrasound beam normal to dovetail load surface 204. Due to refraction through the surfaces of shoe 506 and tooth 122, angles 514 and angle 904 will not be equal. Angle 514, for each shoe 506, in each application is determinable using the particular angle 904 for the tooth design being inspected and the refractive index of the beam path of ultrasound beam 516. In the exemplary embodiment, transducer 502 is manually positioned on outer tooth surface 112 adjacent to the butt joint location. Beam 516 is swept toward the butt joint to inspect the area for cracking. The inspection is performed from both sides of the butt joint location.

The above-described embodiments of ultrasound inspection and test system provide a cost-effective and reliable means for inspecting and/or servicing equipment. More specifically, the ultrasound system is configured to facilitate positioning an ultrasound transducer proximate a workpiece, for example, a generator rotor, and to facilitate operating the test and/or inspection transducer to identify and locate anomalies, such as cracks in the rotor teeth. As a result, the methods and apparatus described herein facilitate testing in a cost-effective and reliable manner.

Exemplary embodiments of ultrasound inspection and test systems are described above in detail. The systems are not limited to the specific embodiments described herein, but rather, components of each system may be utilized independently and separately from other components described herein. Each system component can also be used in combination with other system components.

While the invention has been described in terms of various specific embodiments, those skilled in the art will recognize that the invention can be practiced with modification within the spirit and scope of the claims.

What is claimed is:

1. An inspection system for inspecting a generator rotor comprising:
    a phased-array ultrasound transducer comprising an active face including a plurality of transducer elements formed in an array, said elements configured to be excited in a predetermined sequence to generate a transmission beam of ultrasound energy at a plurality of angles with respect to the active face and configured to be swept through an inspection area, said elements configured to receive ultrasound echoes through the active face; and
    a wedge-shaped shoe comprising a coupling face configured to couple to said transducer and a transmission face configured to couple to the rotor, said shoe configured to refract the ultrasound transmission beam at a predetermined angle at said transmission face such that the beam enters the component at an angle substantially normal to a load surface of the rotor; wherein said coupling face and said transmission face define a plurality of angles including a first angle selected based on a range of angles oriented such that the ultrasound transmission beam is steered along the load surface of the rotor in a substantially axial direction.

2. A system in accordance with claim 1 wherein said load surface is configured to couple to a rotor slot wedge.

3. A system in accordance with claim 1 wherein the rotor includes a plurality of circumferential grooves and a respective land positioned between adjacent grooves and wherein said transducer is sized to couple to the rotor within a groove machined into an outer periphery of the rotor.

4. A system in accordance with claim 1 wherein the rotor includes a plurality of circumferential grooves and a respective land positioned between adjacent grooves and wherein said transducer is sized to couple to an outer periphery of the rotor on the land.

5. A system in accordance with claim 1 wherein said plurality of angles further includes a second angle selected based on an angle between the load surface and the transmission surface, and an ultrasound refractive index of the transducer wedge material.

6. A method of inspection of a rotor of an electrical generator comprising:
    coupling an active face of an ultrasound transducer to a substantially wedge-shaped shoe, the transducer including a plurality of transducer elements formed in an array;
    exciting the plurality of transducer elements to generate an ultrasonic transmission beam; steering the ultrasonic transmission beam along a selected ray path over a range of angles oriented relative to a surface normal;
    transmitting the ultrasonic beam through the shoe such that the ultrasonic beam is refracted to an angle substantially normal to a load surface in the rotor; and
    sweeping the ultrasonic beam through an inspection area.

7. A method in accordance with claim 6 further comprising:
    receiving a plurality of echo signals from the rotor; and
    determining a density interface in the rotor using the plurality of echo signals.

8. A method in accordance with claim 7 wherein receiving a plurality of echo signals from the rotor comprises processing the echo signals in a plurality of channels.

9. A method in accordance with claim 6 wherein exciting the plurality of transducer elements comprises applying a separate excitation signal pulse to each of the transducer elements.

10. A method of inspection of an electrical generator rotor comprising:
    positioning an active face of an ultrasound transducer along a surface of the generator rotor, the transducer including a plurality of transducer elements formed in an array;
    exciting the plurality of transducer elements to produce an ultrasonic transmission beam transmitted into the generator rotor along a selected ray path from the array;

steering the ultrasonic transmission beam along the selected ray path over a range of angles oriented relative to a surface normal;

sweeping the ultrasonic beam through an inspection area;

receiving a plurality of echo signals from the generator rotor using the plurality of transducer elements as receive elements; and determining a density interface indicative of a crack in the generator rotor using the plurality of echo signals.

11. A method in accordance with claim 10 wherein receiving a plurality of echo signals from the generator rotor comprises processing the echo signals in a plurality of channels.

12. A method in accordance with claim 10 wherein exciting the plurality of transducer elements comprises applying a separate excitation signal pulse to each of the transducer elements.

13. A method in accordance with claim 10 wherein the rotor includes a plurality of slot wedges restrained by a load surface of the rotor, the slot wedges oriented end to end in abutted contact with each adjacent slot wedge and wherein positioning an active face of an ultrasound transducer wit respect to a surface of the generator rotor comprises:

positioning the active face on a first side of a butt joint and sweeping the ultrasonic transmission beam toward the butt joint; and positioning the active face on a second side of the butt joint and sweeping the ultrasonic transmission beam toward the butt joint, the second side being axially displaced from the first side.

14. A method in accordance with claim 13 wherein the rotor includes a plurality of circumferential grooves and wherein positioning the active face on a first side of a butt joint located at a groove comprises:

positioning the active face on a first side of the butt joint in the groove, and sweeping the ultrasonic transmission beam toward the butt joint; and positioning the active face on a second side of the butt joint in the groove and sweeping the ultrasonic transmission beam toward the butt joint, the second side being axially displaced from the first side.

15. A method in accordance with claim 13 wherein the rotor includes a plurality of circumferential grooves spaced apart by lands and wherein positioning the active face on a first side of a buff joint located at a groove comprises:

positioning the active face on a land adjacent the groove on a first side of the butt joint, and sweeping the ultrasonic transmission beam toward the butt joint; and positioning the active face on a land adjacent the groove on a second side of the butt joint in the groove and sweeping the ultrasonic transmission beam toward the butt joint, the second side being axially displaced from the first side.

16. A method in accordance with claim 13 wherein the rotor includes a plurality of circumferential grooves spaced apart by lands and wherein positioning the active face on a first side of a butt joint located at a land comprises:

positioning the active face on a first side of the butt joint in the groove, and sweeping the ultrasonic transmission beam toward the butt joint; and positioning the active face on a second side of the butt joint in the groove and sweeping the ultrasonic transmission beam toward the butt joint, the second side being axially displaced from the first side.

17. A method in accordance with claim 13 wherein the rotor includes a plurality of circumferential grooves spaced apart by lands and wherein positioning the active face on a first side of a butt joint located at a land comprises:

positioning the active face on the land on a first side of the butt joint, and sweeping the ultrasonic transmission beam toward the butt joint; and positioning the active face on a second side of the butt joint on the land and sweeping the ultrasonic transmission beam toward the butt joint, the second side being axially displaced from the first side.

* * * * *